United States Patent [19]

Chamberlin

[11] 4,039,547
[45] Aug. 2, 1977

[54] 24-METHYL-14A-AZA-D-HOMO-CHOLEST-8(9)-ENES

[75] Inventor: James W. Chamberlin, Indianapolis, Ind.

[73] Assignee: Eli Lilly and Company, Indianapolis, Ind.

[21] Appl. No.: 655,172

[22] Filed: Feb. 4, 1976

Related U.S. Application Data

[63] Continuation-in-part of Ser. No. 503,562, Sept. 6, 1974, abandoned.

[51] Int. Cl.$^2$ .................. C07D 215/06; C07D 215/08
[52] U.S. Cl. ...................... 260/287 AZ; 260/289 AZ; 424/258
[58] Field of Search .................. 260/287 AZ, 289 AZ

[56] References Cited

U.S. PATENT DOCUMENTS

| | | | |
|---|---|---|---|
| 2,738,350 | 3/1956 | Mazur | 260/289 AZ |
| 3,845,203 | 10/1974 | Williams et al. | 260/289 AZ |
| 3,947,453 | 3/1976 | Jones | 260/287 AZ |
| 3,972,884 | 8/1976 | Jones | 260/289 AZ |
| 3,972,884 | 8/1976 | Jones | 260/287 AZ |
| 4,001,246 | 1/1977 | Jones | 260/289 AZ |
| 4,008,238 | 2/1977 | Jones | 260/287 AZ |

OTHER PUBLICATIONS

Tsuda, "J.A.C.S.," vol. 78, 4107 (1956).

*Primary Examiner*—Donald G. Daus
*Assistant Examiner*—David E. Wheeler
*Attorney, Agent, or Firm*—Charles W. Ashbrook; Everet F. Smith

[57] ABSTRACT

Reduction of 24-methylene-14a-aza-D-homo-cholesta-8(9), 14(14a)-dienes provides new antifungal agents.

8 Claims, No Drawings

24-METHYL-14A-AZA-D-HOMO-CHOLEST-8(9)-ENES

CROSS-REFERENCES TO RELATED APPLICATIONS

This is a continuation-in-part of Application Ser. No. 503,562, filed Sept. 6, 1974, now abandoned.

BACKGROUND OF THE INVENTION

A large number of agents which are effective in controlling various infectious diseases are currently available and in use. Even with these many useful pharmacological agents available, there still remains an alarming number of diseases which plague mankind, many of which are not readily controlled. Infectious diseases caused by the pathogenic fungi is a typical example of poorly controlled diseases. In particular, certain diseases attributed to various species of Candida, including *C. tropicalis* and *C. albicans*, are not easily controlled. It is therefore an object of research scientists to discover new agents which will be effective in the treatment of hard to control diseases, such as those of fungal origin for example.

It is an object of this invention to provide new compounds which are valuable as antifungal agents.

SUMMARY OF THE INVENTION

The present invention relates to new steroid-like compounds that are useful as pharmacological agents and to methods for their preparation. More particularly, this invention is directed to aza-steroid compounds having the formula

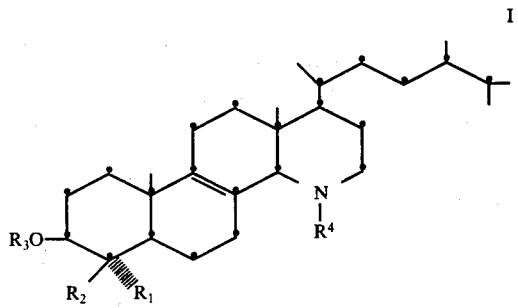

I in which $R_1$ and $R_2$ are both hydrogen or both methyl; $R_3$ is hydrogen, alkanoyl, alkoxycarbonyl, or haloalkoxycarbonyl; and $R_4$ is hydrogen, alkyl, alkanoyl, alkoxycarbonyl, or haloalkoxycarbonyl.

DETAILED DESCRIPTION OF THE INVENTION

This invention provides novel steroid-like compounds having the above formula. The compounds are useful pharmacological agents, especially as antifungal agents.

In the present specification and claims, the term "alkanoyl" refers to carboxylic acid residues with from 1 to 4 carbon atoms. Examples of $C_1$–$C_4$ alkanoyl groups include formyl, acetyl, n-butyryl, and isobutyryl. Examples of alkoxycarbonyl include $C_1$–$C_4$ alkoxycarbonyl groups such as methoxycarbonyl, ethoxycarbonyl, tert-butoxycarbonyl, and the like. The term "halo" as used herein refers to fluoro, chloro, bromo, or iodo, and haloalkoxycarbonyl groups are the $C_1$–$C_4$ alkoxycarbonyl groups bearing halo substituents. Typical halo $C_1$–$C_4$ alkoxycarbonyl groups include chloromethoxycarbonyl, 2-bromoethoxycarbonyl, 2,2,2,-trichloroethoxycarbonyl, 2-bromoisobutoxycarbonyl, and related groups. Typical alkyl groups represented by $R_4$ in the above formula are $C_1$–$C_4$ alkyl groups such as methyl, ethyl, propyl, isobutyl, and the like.

The preferred compounds of this invention are represented by the above formula wherein $R_3$ is hydrogen or $C_1$–$C_4$ alkanoyl, and $R_4$ is hydrogen or $C_1$–$C_4$ alkanoyl.

The organic bases of this invention form pharmaceutically acceptable salts with a variety of inorganic and strong organic acids including sulfuric, hydrochloric, hydrobromic, phosphoric, citric, lactic, maleic, succinic, cinnamic, acetic, benzoic, gluconic, ascorbic, and related acids. The bases additionally form quaternary ammonium salts with a variety of alkylating agents such as sulfates, alkylhalides, and sulfonates. Such agents include methyl chloride, ethyl bromide, allyl bromide, isobutyl iodide, benzyl chloride, dimethyl sulfate, methyl benzenesulfonate, ethyl toluenesulfonate, and the like. It will be recognized that salt formation with the organic bases of the invention occurs most readily when $R_4$ of the above formula is hydrogen or an alkyl group.

The compounds of this invention are prepared by catalytically reducing a naturally occurring aza-steroid of the formula

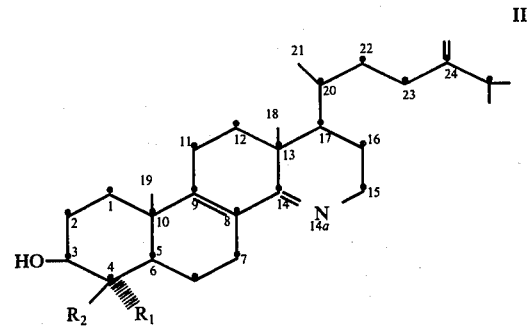

II in which $R_1$ and $R_2$ are both hydrogen or both methyl. The reaction is accomplished by subjecting the triene of the above formula to hydrogen in the presence of a suitable hydrogenation catalyst. The reaction preferably is carried out in a solvent. The reaction is normally carried out at a temperature in the range of about 10° to about 100° C., preferably at about 25° to 35° C. Generally, relatively low hydrogen pressures are maintained during the reaction, thereby precluding exhaustive reduction of the starting triene. The hydrogen pressure typically is maintained at about 15 to about 100 p.s.i., and preferably at about 15 to 25 p.s.i. Examples of suitable catalysts commonly used in the reaction include Raney nickel, platinum, platinum oxide, and palladium. When palladium is used, it can be employed as a finely divided metal either alone or on an inert support such as carbon, alumina, barium carbonate, silica, or the like. The catalyst most commonly used in practice is platinum oxide. For best results, the catalyst is prereduced prior to the hydrogenation. The amount of catalyst used in the reaction is normally about 1.0 mg. of catalyst for each 10.0 mg. of substrate; however, the precise amount of catalyst is not critical and more, or less, can be used if desired. When lesser amounts of catalyst are employed, longer reaction times are generally needed for the desired reduction to be completed. The hydrogenation can best be carried out in a suitable solvent. Any of a number of solvents can be employed for the reaction, however, the solvent selected is preferably one in which the substrate is substantially soluble and one which is generally unreactive toward hydrogenation. Typical solvents commonly used include ethers such as tetrahydrofuran or dioxane; alcohols such as methanol or ethanol; esters, especially ethyl acetate or methyl acetate; acids such as acetic acid or formic acid; or water. The most preferred solvents include ethyl acetate and tetrahydrofuran. The reaction is generally substantially completed after about 0.5 to about 5 hours, and can be monitored by observing the uptake of hydrogen if desired. The product is isolated by first removing the catalyst, normally by filtration, and concentrating the filtrate to provide the reaction product, generally as an oil or as a solid. Further purification can be accomplished if desired by standard methods such as chromatography, recystallization, salt formation, or the like.

The compounds of this invention are named according to the accepted steroid nomenclature system by following the numbering system shown in the above formula. It should be noted that the compounds of this invention will have the same stereochemistry as the starting material, except at the sites of reduction of unsaturations. For example, all of the compounds described herein will have a 3$\beta$ carbon-oxygen bond, as evidenced in the above formula by the solid bonding line. Additionally, all of the compounds will have a 5$\alpha$ hydrogen atom, as does the starting material. Reduction of the $C_{14}$-$N_{14a}$ unsaturation according to this invention provides a mixture of $\alpha$- and $\beta$-isomers, consisting predominantly of the $\alpha$-isomer. Both isomers, as well as the mixture, are claimed herein, since both isomers have antifungal activity. Reduction of the C-24 methylene group of the starting materials used herein provides an epimeric mixture at C-24. Both the epimers, as well as the epimeric mixture, all of which are useful as antifungal agents, are claimed herein. The nomenclature for the compounds of this invention has been simplified throughout this application by deleting the stereochemical assignments of $\alpha$ and $\beta$. For example, the systematic name of the starting material of the above formula, wherein $R_1$ and $R_2$ are both hydrogen, is 3-hydroxy-24-methylene-14a-aza-D-homo-cholesta-8(9), 14(14a)-diene. Similarly, the corresponding tetrahydro derivative provided by the present invention is 3-hydroxy-24-methyl-14a-aza-D-homo-cholest-8(9)-ene.

The reduced products of the above-described hydrogenation reaction can be further modified, for example by alkylation or acylation, to provide additional antifungal agents. In particular, the 3-hydroxy-24-methyl-aza-cholestene derivatives can be alkylated at the 14a-aza position to provide N-alkyl derivatives. Generally, the alkylation can be accomplished by commingling the aza-cholestene derivative with an alkylating agent in equimolar amounts, preferably in a mutual solvent and in the presence of an acid binding agent, such as triethylamine or potassium carbonate for example. Typical alkylating agents include methyl iodide, methyl sulfate, ethyloxonium tetrafluoroborate, butyl chloride, and the like. The alkylation is generally complete after about 1 to 5 hours when carried out at a temperature of about 25° to 60° C. The N-alkyl derivative can be isolated by removal of the solvent and normal purification, or alternatively, the product can be isolated as an acid addition salt by proper adjustment of the pH.

In a further aspect of the invention, the 3-hydroxy-24-methyl-14a-aza-D-homo-cholest-8(9)-enes can be acylated, with a reactive derivative of a $C_1$-$C_4$ alkanoic acid for example, thereby forming 3-alkanoyloxy-14a-aza-N-acyl derivatives. Acylating agents commonly used include acid halides, especially acid chlorides or acid bromides; acid anhydrides, including mixed acid anhydrides; and ketenes. The acylation reaction is normally carried out by mixing the 3-hydroxy-24-methyl-aza-cholestene of the invention with a 2 to 200 molar excess of an acylating agent, preferably in a mutual solvent such as benzene, N,N-dimethylformamide, dichloromethane, pyridine, triethylamine, or the like, and in the presence of an acid binding agent, such as pyridine or triethylamine for example. The acylation is generally substantially complete after about 2 to 20 hours when carried out at a temperature of about 0° to 50° C. The product, a 3-alkanoyloxy-24-methyl-14a-aza-N-acyl-D-homo-cholestene, is usually isolated by adding water to the reaction mixture and extracting the product therefrom with a water immiscible solvent such as ethyl acetate or diethyl ether, for example. Solvent removal generally provides the desired product as a solid which can be recrystallized if desired.

The 3-alkanoyloxy-24-methyl-14a-aza-N-acyl-D-homo-cholestenes are readily converted to the corresponding 3-hydroxy-24-methyl-14a-aza-N-acyl-D-homo-cholestenes by mild aqueous alkaline hydrolysis of the ester group. In particular, the 3-alkanoyl group is removed by reaction with aqueous bases, such as sodium hydroxide or potassium hydroxide for example. The hydrolysis is generally conducted in a solvent, such as methanol for instance, and is generally complete after about 1 to 4 hours when carried out at a temperature of about 20° to 60° C. The N-acyl group is generally not affected by such hydrolysis conditions.

The 3-alkanoyloxy-24-methyl-14a-aza-D-homo-cholestenes, compounds of Formula I in which $R_3$ is alkanoyl and $R_4$ is hydrogen, are generally prepared by simple transesterification with an appropriate alkanoic acid ester, such as ethyl formate or methyl acetate, for example. The 3-hydroxy-14a-aza-D-homo-cholestenes are stirred in the appropriate alkanoic acid ester for about 2 to 20 hours at a temperature of about 25° to 150° C.

Treatment of the 3-hydroxy-14a-aza-D-homo-cholestenes with acylating agents of the haloformate class, such as $C_1$-$C_4$ alkyl chloroformates or halo $C_1$-$C_4$ alkyl chloroformates for instance, provides the corresponding 3-alkoxycarbonyloxy-14a-aza-N-alkoxycarbonyl-D-homo-cholestene derivatives. These acylations are generally carried out in a mutual solvent such as dichloromethane and in the presence of an acid binding agent, such as triethylamine or pyridine for example. The 3-alkoxycarbonyl groups are readily removed by mild hydrolysis, in preference to the N-alkoxy-carbonyl groups. When the 3-alkoxycarbonyloxy-14a-aza-D-homo-cholestene derivatives are desired, compounds of Formula I in which $R_3$ is alkoxycarbonyl and $R_4$ is hydrogen for example, it is generally preferable to first acylate the triene starting material, and then carry out the hydrogenation reaction in the normal fashion. It should be noted that functionalization of the 3-hydroxy group of the triene starting material can be carried out prior to hydrogenation whenever desired.

Illustrative examples of specific compounds provided by this invention include:

3-Hydroxy-24-methyl-14a-aza-D-homo-cholest-8(9)-ene;

3-Hydroxy-24-methyl-14a-aza-D-homo-4,4-dimethyl-cholest-8(9)-ene;
3-Acetoxy-24-methyl-14a-aza-D-homo-14a-acetyl-cholest-8(9)-ene;
3-Hydroxy-24-methyl-14a-aza-D-homo-14a-isobutyl-cholest-8(9)-ene;
3-Propionyloxy-24-methyl-14a-aza-D-homo-cholest-8(9)-ene;
3-(2,2,2-trichloroethoxycarbonyl)oxy-24-methyl-14a-aza-D-homo-14a-2,2,2-trichloroethoxycarbnyl-cholest-8(9)-ene;
3-Hydroxy-24-methyl-14a-aza-D-homo-14a-methoxycarbonyl-cholest-8(9)-ene;
3-Hydroxy-24-methyl-14a-aza-D-homo-14a-methylcholest-8(9)-ene-14a-ium formate;
3-Hydroxy-24-methyl-14a-aza-D-homo-4,4-dimethyl-cholest-8(9)-ene-14a-ium acetate;
3-Hydroxy-24-methyl-14a-aza-D-homo-cholest-8(9)-ene-14a-ium chloride;
3-Hydroxy-24-methyl-14a-azonia-D-homo-14a-methyl-cholest-8(9)-ene iodide;
and the like.

As hereinbefore indicated, the starting materials required for preparing the compounds of this invention are 24-methylene-14a-aza-D-homo-cholesta-8(9), 14(14a)-diene derivatives. These triene substances are prepared by culturing the strain of *Geotrichum flavo-brunneum*, NRRL 3862, which strain is in the permanent culture collection of the Agricultural Research Service, Northern Utilization Research and Development Division, Department of Agriculture, Peoria, Illinois. The organism which is cultured was isolated by the standard serial dilution procedure from a soil sample collected in the Grand Teton National Park region of Wyoming. The organism is described in detail by Miller, et al., Mycologia, 49, 779-808, 1957. The preparation and isolation of the starting material used in the present invention is the subject of U.S. Pat. No. 3,845,203 and is carried out as described hereinbelow.

A culture of *Geotrichum flavo-brunneum* is grown under submerged aerobic conditions in a fermentation medium comprising carbohydrates, amino acids, and nutrient inorganic salts. The organism is grown for about 3 days at a temperature of about 20° to 35° C. After the fermentation is complete, the fermentation mycelium is extracted with a suitable organic solvent, such as ethyl acetate or amyl acetate for instance. Evaporation of the solvent from the combined organic extracts provides a mixture of compounds. The starting materials for the present invention are separated from the mixture by chromatography and crystallization.

The compounds provided by this invention are useful for combating infections of fungal origin. Such compounds have demonstrated useful in vitro activity when tested in a standard disc plate assay employing organisms such as *Candida albicans* and *Trichophyton mentagraphytes*. For example, 3-hydroxy-24-methyl-14a-aza-D-homo-cholest-8(9)-ene demonstrated a minimum inhibitory concentration (MIC) of 1.25 μg/ml. when tested against *C. albicans* and an MIC of 0.078 μg/ml. against *T. mentagraphytes*.

The compounds provided herein can be suitably formulated and applied to various surfaces infected with fungal growth in order to control such growth. For example, the compounds of this invention control fungal growth when applied to environmental surfaces such as shower stalls, foot baths, exterior surfaces of wood, concrete, brick, as well as to skin surfaces affected by such fungal growth. The compounds are most conveniently formulated for use as a solution, spray, suspension, powder, or the like, by being admixed with common diluents, excipients and carriers. Commonly used diluents, excipients and carriers include water, ethanol, propylene glycol, mannitol, cellulose, starch powder, sodium benzoate and the like. An example of a typically formulated compound of this invention comprises from about 0.5 to 5.0 grams of a compound such as 3-hydroxy-24-methyl-14a-aza-D-homo-14a-formyl-cholest-8(9)-ene dissolved in about 500 to 1,000 cc. of water. Such solution can be added to a shower stall or foot bath in order to control fungal growth, particularly that attributable to Candida organisms.

A compound of this invention can alternatively be formulated as a cream or ointment for convenient application to skin surfaces infected with fungal growth. For example, a compound such as 3-hydroxy-24-methyl-14a-aza-D-homocholest-8(9)-ene hydrochloride in the amount of about 500 mg. is admixed with from 500 to 1,000 mg. of a suitable carrier such as lanolin, cold cream, or white petrolatum. Such mixture can be applied to an infected skin surface at the rate of about 1 to 5 mg. per square centimeter of skin surface in order to control fungal growth.

The following detailed examples are presented for the purpose of illustration only and are not to be construed as limiting the invention in scope. In general, the compounds described hereinbelow were characterized by mass spectral analysis, melting point, and infrared absorptions, given in wave numbers (cm$^{-1}$).

Preparation 1

The production of the starting materials required for the present invention is illustrated by the following procedure.

Spores of *Geotrichum flavo-brunneum* strain NRRL 3862 were inoculated on a nutrient agar slant having the following composition:

| Agar Slant Medium | |
| --- | --- |
| Ingredient | Weight/Volume (g./l.) |
| Glucose | 20 |
| Peptone | 5 |
| Potassium Dihydrogen Phosphate | 0.5 |
| Magnesium Sulfate | 0.02 |
| Ferrous Sulfate | 0.01 |
| Agar | 20 |

The above cultures were incubated at a temperature of 25° C. for 7 days. A loop of spores from the slant culture was transferred to a vegetative inoculum having the following composition:

| Vegetative Medium | |
| --- | --- |
| Ingredient | Weight/Volume (g./l.) |
| Sucrose | 25 |
| Edible Molasses | 36 |
| Corn Steep | 6 |
| Potassium Dihydrogen Phosphate | 2 |
| NZ Case[1] | 10 |
| Tap Water | |

[1]Enzymatic digest of casein, Scheffield Chemical Co., Norwich, N.Y.

The inoculated vegetative medium was shaken on a rotary shaker at 250 r.p.m. for about 24 to 48 hours at a temperature of about 25° C. Five percent of the volume of the vegetative inoculum containing viable vegetative growth was employed to inoculate a fermentation medium having the following composition:

| Fermentation Medium | |
|---|---|
| Ingredient | Weight/Volume (g./l.) |
| Glucose | 25 |
| Corn Starch | 10 |
| Peptone (meat) | 10 |
| NZ Amine A[1] | 4 |
| Molasses | 5 |
| Magnesium Sulfate Heptahydrate | 5 |
| Calcium Carbonate | 2 |
| Tap Water | |

[1]Pancreatic hydrolysate of casein, Scheffield Chemical Company, Norwich, N.Y.

The inoculated fermentation medium was agitated continuously for 72 hours at a temperature of 25° C. Throughout the fermentation, sterile air was passed through the fermentation medium at a rate of one half volume of air per volume of fermentation medium per minute.

Upon completion of the fermentation, the fermentation broth was extracted several times with ethyl acetate. The combined ethyl acetate extracts were concentrated to an oil residue. The residue was dissolved in a 20 percent acetone solution in n-hexane. Additional hexane was added to the mixture, and the solution was cooled to −20° C. whereupon 3-hydroxy-24-methylene-14a-aza-D-homo-chloesta-8(9), 14(14a)-diene crystallized. The crystals were collected by filtration and air dried, m.p. 115°-118° C. The filtrate was concentrated to dryness, providing an oily residue which was dissolved in a mixture of ethyl acetate-hexane-distilled water (80:16:4). The solution was passed over a column packed with basic alumina (Woelm grade W200, Water Associates, Inc., Framingham, Mass.). The column was eluted with the same solvent mixture, and eluate fractions of 1 liter volume each were collected. Elutate fractions 9 through 23 were combined and the solvent was removed therefrom under reduced pressure to provide a residue which was crystallized from acetone. The crystals were collected by filtration and identified as 3-hydroxy-24-methylene-14a-aza-D-homo-4,4-dimethyl-cholesta-8(9), 14(14a)-diene, m.p. 147° C.

EXAMPLE 1

3-Hydroxy-24-methyl-14a-aza-D-homo-cholest-8(9)-ene

A suspension of 40 mg. of platinum oxide in 10 cc. of ethyl acetate was stirred under a hydrogen atmosphere at about 15 to 20 p.s.i. for 15 minutes at 25° C. in a Brown hydrogenation apparatus. To the reaction mixture was added a solution of 415 mg. of 3-hydroxy-24-methylene-14a-aza-D-homo-cholesta-8(9), 14(14a)-diene in 5 cc. of ethyl acetate. The reaction mixture was stirred at 25° C. for 1 hour with the hydrogen pressure maintained at about 20 p.s.i. The reaction mixture was filtered and the filtrate was concentrated to dryness under reduced pressure, affording 316 mg. of essentially pure 3-hydroxy-24-methyl-14a-aza-D-homo-cholest-8(9)-ene. m/e; M+ 415.

EXAMPLE 2

3-Hydroxy-24-methyl-14a-aza-D-homo-cholest-8(9)-ene-14a-ium chloride.

A solution of 3-hydroxy-24-methyl-14a-aza-D-homo-cholest-8(9)-ene dissolved in diethyl ether was stirred at room temperature while excess hydrogen chloride gas was bubbled through the solution. The product crystallized out of solution and was collected by filtration, providing 3-hydroxy-24-methyl-14a-aza-D-homo-cholest-8(9)-ene as the hydrochloride salt.

EXAMPLE 3

3-Acetoxy-24-methyl-14a-aza-D-homo-14a-acetyl-cholest-8(9)-ene.

A solution of 595 mg. of 3-hydroxy-24-methyl-14a-aza-D-homo-cholest-8(9)-ene in 10 cc. of acetic anhydride containing 10 cc. of pyridine was stirred at 25° C. for 16 hours. The reacton mixture was added to 100 cc. of water, and the aqueous mixture was extracted several times with diethyl ether. The ethereal extracts were combined, washed successively with 1N hydrochloric acid, water, and saturated aqueous sodium chloride solution, and dried. Removal of the solvent under reduced pressure provided 659 mg. of an oil which was crystallized from hexane, affording 3-acetoxy-24-methyl-14a-aza-D-homo-14a-acetylcholest-8(9)-ene, m.p. 127°-132° C. m/e: M+ 499.

IR (CHCl$_3$): 1640 cm$^{-1}$ (amide); 1721 cm$^{-1}$ (ester).

I claim:

1. A compound of the formula

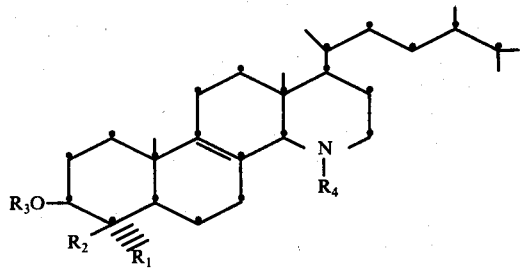

wherein:
$R_1$ and $R_2$ are both hydrogen or both methyl;
$R_3$ and $R_4$ independently are hydrogen or $C_1$–$C_4$ alkanoyl;
and the pharmaceutically acceptable salts thereof.

2. The compound of claim 1 wherein $R_1$ and $R_2$ are both hydrogen.

3. The compound of claim 1 wherein $R_3$ and $R_4$ are both hydrogen.

4. The compound of claim 3, said compound being 3-hydroxy-24-methyl-14a-aza-D-homo-cholest-8(9)-ene.

5. The compound of claim 4 as the pharmaceutically acceptable acid addition salt.

6. The compound of claim 1 wherein $R_3$ and $R_4$ are both $C_1$–$C_4$ alkanoyl.

7. The compound of claim 6, said compound being 3-acetoxy-24-methyl-14a-aza-D-homo-14a-acetyl-cholest-8(9)-ene.

8. The compound of claim 1 wherein $R_3$ is hydrogen and $R_4$ is $C_1$–$C_4$ alkanoyl.